(12) United States Patent
Bass (10) Patent No.: US 6,918,903 B2
(45) Date of Patent: *Jul. 19, 2005

(54) DEVICE FOR SUCTION-ASSISTED LIPECTOMY AND METHOD OF USING SAME

(75) Inventor: Lawrence S. Bass, Great Neck, NY (US)

(73) Assignee: Starion Instrument Corporation, Saratoga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/410,315

(22) Filed: Apr. 8, 2003

(65) Prior Publication Data

US 2003/0176851 A1 Sep. 18, 2003

Related U.S. Application Data

(63) Continuation of application No. 09/415,543, filed on Oct. 8, 1999, now Pat. No. 6,544,248, which is a continuation of application No. 08/908,455, filed on Aug. 7, 1997, now Pat. No. 6,102,885.

(60) Provisional application No. 60/022,497, filed on Aug. 8, 1996.

(51) Int. Cl.$^7$ ............................................. A61M 31/00
(52) U.S. Cl. ...................................... 604/511; 604/22
(58) Field of Search ............................ 604/20, 22, 35, 604/39, 43, 500, 511, 118, 131, 902, 503; 606/41, 49, 50

(56) References Cited

U.S. PATENT DOCUMENTS

| | | | |
|---|---|---|---|
| 2,275,167 A | 3/1942 | Bierman | 606/50 |
| 3,828,780 A | 8/1974 | Morrison, Jr. | 128/275.1 |
| 3,902,494 A | * 9/1975 | Haberlen et al. | 604/20 |
| 4,674,499 A | * 6/1987 | Pao | 604/20 |
| 5,112,302 A | 5/1992 | Cucin | 604/35 |
| 5,195,959 A | 3/1993 | Smith | 604/34 |
| 5,300,069 A | 4/1994 | Hunsberger et al. | 606/46 |
| 5,348,535 A | 9/1994 | Cucin | 604/35 |
| 5,401,272 A | 3/1995 | Perkins | 606/15 |
| 5,419,761 A | 5/1995 | Narayanan et al. | 604/22 |
| 5,441,498 A | 8/1995 | Perkins | 606/15 |
| 5,514,086 A | 5/1996 | Parisi et al. | 604/22 |
| 5,562,609 A | 10/1996 | Burmbach | 604/35 |
| 5,643,304 A | 7/1997 | Schechter et al. | 604/22 |
| 5,669,876 A | 9/1997 | Schechter et al. | 604/35 |
| 5,685,877 A | 11/1997 | Pagedas et al. | 606/46 |
| 5,718,709 A | 2/1998 | Considine et al. | 606/46 |
| 6,102,885 A | * 8/2000 | Bass | 604/22 |
| 6,544,248 B1 | * 4/2003 | Bass | 604/511 |

OTHER PUBLICATIONS

Oct. 1996 Ultrasonic Assisted Lipoplasty by Michele L. Zocchi.
Oct. 1996 Results of Multicenter Study of Laser–Assisted Liposuction by David B. Apfelberg.
Oct. 1996 History and Current Concepts of Lipoplasty by Yves–Gerard Illouz.

* cited by examiner

Primary Examiner—Manuel Mendez
(74) Attorney, Agent, or Firm—K. David Crockett, Esq.; Crockett & Crockett (57) ABSTRACT

A device is described which allows simultaneous application of suction or vacuum for evacuation of fat with application of energy to the fat inside an opening in a cannula. A pair of electrodes is situated within the cavity of the cannula just under the surface of cannula tip opening(s) or as part of the walls of such openings. The electrodes are spaced to allow coagulation of fat entering the cannula. Irrigation may be applied in a continuous or discontinuous or intermittent stream within the cannula to cool the tip and facilitate removal of suctioned tissue and prevent buildup of debris on electrodes. A method for using the cannula to remove adipose tissue or fat destroyed by the energy application through the use of suction with mechanical motion of the cannula, with energy application and optionally with the use of irrigation is also disclosed.

9 Claims, 3 Drawing Sheets

FIG. 1

DEVICE FOR SUCTION-ASSISTED LIPECTOMY AND METHOD OF USING SAME

This application is a continuation of Ser. No. 09/415,543 filed Oct. 8, 1999, now U.S. Pat. No. 6,544,248, which is a continuation of Ser. No. 08/908,455 filed Aug. 7, 1997, now U.S. Pat. No. 6,102,885, which claims priority to U.S. Provisional Application 60/022,497, filed Aug. 8, 1996.

FIELD OF THE INVENTIONS

The present invention generally relates to a device and method for suction-assisted lipectomy utilizing a cannula or hollow tube having at least one opening at a distal end and means for attaching a suction source at the proximal end, more particularly, to a device and method having at least one energy conductive element on or within or as an integral part of the device connected to energy transferring means for transferring energy to tissue drawn within the opening by suction or mechanical effect of passing the cannula back and forth in the tissue, and most particularly, relates to devices and methods for simultaneous application of suction or vacuum and energy to adipose fat during lipectomy surgery to expedite the evacuation of the adipose fat from the surgical site.

BACKGROUND OF THE INVENTIONS

Traditional aesthetic surgical approaches to excess collections of adipose tissue have involved open surgical excision of the fat and overlying skin in the affected region. Such dermolipectomy was effective but had significant recovery time and placed a visible scar, often of substantial size, at the surgical site.

More recently, suction-assisted lipectomy has been used. In this technique, a thin cannula of metal or plastic or composite material is advanced along the area of fat collection through a small stab incision (5–10 mm) in the skin. This cannula is passed back and forth to traverse the entire area of fat in which reduction is desired. Often this will be done from more than one access incision surrounding the same area to provide a different angle for the passes with the cannula. During the insertion and removal of the cannula, suction is applied through the lumen of the cannula. This allows fat to be drawn in through the openings in the tip of the cannula which then breaks fat globules off by virtue of the suction action or by motion of the cannula hole edges against the fat or both or other actions. Additional fat is damaged by the suction or bruising or cutting action of the cannula which produces cell death or necrosis of fat in situ in addition to that fat which is physically removed thorough the cannula. This controlled in situ tissue injury adds to the contour improvement by providing additional loss of fat and may aid in skin contraction/scarring.

Further improvements have taken place in adjunctive techniques for suction-assisted lipectomy. These include use of the "tumescent technique." This technique involves the infusion of large amounts of a very dilute anesthetic/vasoconstrictor solution into the tissues prior to use of the suction cannula. This is thought to increase the rate and completeness of fat removal, decrease blood loss, and post-operative bruising and recovery time. In addition, anesthesia following this wide infiltration of the solution is protracted. The volume of fluid added reduces the need for large amounts of intravenous infusion and allows larger volumes of fat to be suctioned due to the reduced blood loss.

Cannulas have been developed which incorporate additional features besides openings at the tip to allow application of suction. Cannulas which have ultrasonic generators at the tip are believed to be under development. These cannulas are thought to allow increased fat removal due to disruption of fat cells by the sound waves produced by the ultrasonic element in the tip. The energy used is applied or transmitted external the cannula into the fat surrounding the cannula tip (See Zocchi M C: Ultrasonic assisted lipoplasty: Technical refinement and clinical evaluations; Clinics in Plastic Surgery (203(4): 575–598, 1996). The sound producing element is stated to produce a smoother skin contour due to more even removal of fat cells. The technique is slow requiring much more time than traditional suction alone techniques. The tip tends to become hot creating a risk of burning the skin.

Laser devices have been tested for suction-assisted lipectomy, (see Apfelberg D B: Results of a multicenter study of laser-assisted liposuction, Clinics in Plastic Surgery 23(4): 713–720, 1996). These laser devices fire a laser fiber just proximal to the opening in the cannula across the space just deep to the opening in the cannula. This design appears to fire the laser in the fat that is about to be drawn into the opening in the cannula, such as a single hole device. While some contact may take place between the laser fiber and the fatty tissue, the system appears to be designed for delivery of light energy to the fat without direct contact with the fat being required.

An overview reference of currently available liposuction technology is contained in Illouz Y G: History and current concepts of lipoplasty, Clinics in Plastic Surgery 23(4): 721–730, 1996.

Prior art patents disclosing prior devices include bipolar electrode probe devices for use in electro-cautery and electro-coagulation. One patent relating to an Electro-Surgical Instrument is U.S. Pat. No. 2,275,167 issued to Bierman. This patent describes an electro-surgical device which is designed to coagulate or ablate tissue in order to destroy tissue. A suction cup shaped cavity is produced to draw the tissue into the electrode area of the device. The device is not configured to provide a conduit for removal of the tissue through the device.

A Combined Electro-Coagulator-Suction Instrument is disclosed in U.S. Pat. No. 3,828,780, issued to Morrison. This patent defines an instrument with a non-insulated tip which is connected electrically to a source of electrical current through a second channel separate from the channel for applying suction. The combined instrument has a source of current which is exposed on the external surface of the device, is oriented at the distal end of the device coaxially with the suction and does not provide a source of irrigation. It is believed that the Morrison device would be unsuitable for use in lipectomy surgery and in fact is intended not for removal of tissue but for aspiration of blood to allow proper action of the coagulation to obtain hemostasis.

A Suction Surgical Instrument is disclosed in U.S. Pat. No. 3,902,494 issued to Haberlen. This patent describes a device with a monopolar electrode which is, in the preferred embodiment, ring shaped on the external surface of the tip of the device in communication with a suction channel. There appears to be an external application of current. The device appears to be monopolar and not bipolar and there is no apparent provision for irrigation.

An example of a Co-axial Bipolar Probe is illustrated by U.S. Pat. No. 4,674,499 issued to Pao. This patent describes a bipolar electrode probe device for use in electro-cautery and electro-coagulation having a central electrode which is described as protrusive beyond the insulating sheath. The device has a single channel which may be used for irrigation or alternatively placed under vacuum. Thus, a single lumen does not appear to provide for the simultaneous application of fluid irrigation and vacuum. Also, the lumen appears to be centrally positioned and the spacing of the distance between the electrodes, about 0.2 to about 0.45 mm, is believed substantially smaller than needed for utilization in suction assisted lipectomy.

An Electro-Surgical Device with Suction and Irrigation is disclosed in U.S. Pat. No. 5,195,959, issued to Smith. The Electro-Surgical Device described therein includes a means of providing mono-polar electro-cautery current in combination with the ability to produce suction of fluid or blood in the field and irrigation introduced into the surgical field. The orientation and configuration of the device appears to apply irrigation or electrical current to the surgical field itself.

A device and a method of Using a Multi Modality Probe With Extendable Bipolar Electrodes is disclosed in U.S. Pat. Nos. 5,401,272 and 5,441,498 issued to Perkins. The method described appears to employ a device which may have suction, electrical source, an irrigation source and a laser source. The device appears to be designed for cutting and then coagulating tissue. The electrodes of the device are movable extending to the exterior of the device.

Thus, there is a need for devices and methods for performing suction assisted lipectomies which, due to the coagulation effect of the electrocautery, accomplishes faster and more complete fat removal; obtains better hemostasis, produces less bruising, less blood loss and faster patient recovery; costs less than ultrasonic or laser liposuction cannulas; when the device is manufactured as a disposable device, given the difficulty of cleaning and sterilizing hollow instruments, reduces infection risks and uses bipolar electrocautery to minimize the risk of spark gap injury, skin burns or other complications from overexposure or unintended tissue exposure to electrical energy.

SUMMARY

It is an object of the present invention to provide a surgical device and method which will allow suction-assisted lipectomy with the simultaneous application of electrical energy via electrodes located within the cannula lumen but beneath the cannula tip entry aperture(s)

Another object of the present invention is to provide a device and a method for reducing recovery time for lipectomy surgery.

A further object of the present invention is to provide a device and a method for applying irrigation simultaneously to the energy transfer elements or electrodes and the suction lumen.

A still further object of the present invention is to provide a device and a method for reducing the size of the visible scar at the surgical site.

Another object of the present invention is to provide a device and a method where the electrodes are located within the insulating cavity and are not directly in contact with tissue on the external surface of the device or external the device.

One preferred embodiment of the device of the present invention uses energy transferring means, such as, for example, bipolar electrocautery current, with monopolar electrocautery, high frequency electrical diathermy or other forms of continuous, discontinuous, pulsed or interrupted applications of electrical energy being possible alternatives, applied to tissue. The energy is applied to the tissue after the tissue has been drawn into a hollow channel by a suction means. The size of the devices of the present invention range from, including, but not limited to, about ten (10) to about fifty (50) centimeters (cm) in length with an outer diameter of about one (1) to about twenty (20) mm.

The method of using the device of the present invention incorporates the traditional technique of using conventional liposuction cannulas. The cannula is passed into the subcutaneous fat space through a small incision in the skin. The cannula is then advanced and withdrawn creating a pass of the cannula through part of the area of desired contour reduction. Sequential passes are made to provide suctioning and reduction of the entire area. The method of the present invention includes the application of energy using the device of the present invention before, during or after the suctioning step. In the preferred method, this will be done continuously or discontinuously during suctioning. Optionally, irrigation within the cannula to cool the tip and facilitate removal of debris will be performed during suctioning.

One representative device for suction assisted lipectomy comprises: a hollow cannula having at least one opening in the distal end and means for connecting the cannula to a negative pressure source at the proximal end; a handle for use by a surgeon to direct and control the distal end in the surgical site and advance the cannula into and withdraw the cannula from the surgical site with the required control and force; and energy transferring means, operatively positioned proximate the opening and operatively connected to an energy source, for transferring energy to adipose tissue drawn into the cannula through the at least one opening.

Another representative device for suction assisted lipectomy comprises: a hollow cannula having at least one opening in the distal end and means for connecting the cannula to a negative pressure source at the proximal end; a handle for use by a surgeon to direct and control the distal end in the surgical site and advance the cannula into and withdraw the cannula from the surgical site with the required control and force; energy transferring means, operatively positioned proximate the opening and operatively connected to an energy source, for transferring energy to adipose tissue drawn into the cannula through the at least one opening; and means, operatively connected to the cannula, for delivering irrigation fluid to the vicinity of the energy transferring means.

One representative method for performing a lipectomy comprises the steps of: providing a device comprising: a hollow cannula having at least one opening in the distal end and means for connecting the cannula to a negative pressure source at the proximal end; a handle for use by a surgeon to direct and control the distal end in the surgical site and advance the cannula into and withdraw the cannula from the surgical site with the required control and force; energy transferring means, operatively positioned proximate the opening and operatively connected to an energy source, for transferring energy to adipose tissue drawn into the cannula through the at least one opening; and means, operatively connected to the cannula, for delivering irrigation fluid to the vicinity of the energy transferring means; inserting the device through relatively small skin incisions to gain access to the subcutaneous fatty tissue to be removed; maneuvering the device into and out of the tissue in order to traverse a large area of the fatty tissue in successive passes of the device in and out along the long axis of the device; simultaneous with the maneuvering motion by the surgeon, applying suction through a suction channel formed in the cannula; applying energy to the energy transfer means during the advancement and withdrawal of the cannula; and irrigating to provide cooling for the energy transferring means and the opening and to reduce buildup of debris around the energy transferring means and within the cannula.

The device and method described by the present invention have several advantages compared with the original suction-assisted lipectomy technique as well as the improvements of tumescent liposuction and ultrasonic liposuction. Due to the coagulation effect of the electrocautery, faster and more complete fat removal is produced. Better hemostasis is obtained, producing less bruising, less blood loss and faster recovery. The device is lower cost than ultrasonic or laser liposuction cannulas. The device may be manufactured as a disposable device reducing infection risks given the difficulty of cleaning and sterilizing hollow instruments. In the preferred embodiment where bipolar electrocautery is used, the risk of spark gap injury, skin burns or other complications from overexposure or unintended tissue exposure to electrical energy are minimized.

Other objectives and advantages of the present application will become apparent from the following description, the accompanying drawings and the appended claims.

DETAILED DESCRIPTION OF THE INVENTIONS

A representative device of the present invention useful with the method of the present invention is fashioned as a long tube or cylinder of plastic or metal or other composite material and may be straight or curved. The material used to make the device must be stiff enough to withstand repeated passes of the cannula within subcutaneous tissue. The outer surface of the cannula may be coated with an additional layer of plastic, Teflon, or similar material to decrease friction during cannula advancement within biological tissue and to prevent adherence of tissue and other material on the cannula.

The cannula tip may be constructed in various forms, including, but not limited to, forked, spherical, oblate, ridged, conical, or otherwise. The cannula tip may have single or multiple opening(s) or aperture(s). The opening(s) may vary in size and shape, including but not limited to, oval, circular, ellipsoid or slit-like. The tip opening(s) may be evenly spaced around the circumference of the cannula, equidistant from the tip, spaced different distances from the tip or all oriented on one side or on multiple sides of the cannula in a variety of patterns. Energy transferring means, such as, for example, electrodes may be placed beneath one or more or all of the opening(s). The electrodes may be equal in size and shape or dissimilar in size and shape between different opening(s). The electrodes are preferably made of an electrically conducting material and may be coated with an additional layer of material such as, for example, Teflon, among others, to prevent adherence of char and tissue debris thereto. The electrodes may be integrated into the wall of the opening(s) to allow application of current on the surface of the device.

The device of the present invention may be reusable or disposable. Sterilization of the device is possible using the customary steam, radiation, or ethylene oxide (gas) techniques, as is known in the art.

The presently preferred embodiment of the device is illustrated as a bipolar delivery of electrical energy. Alternative energy delivery methods contemplated for treating the adipose tissue or fat abutting the electrodes with heat include, but are not limited to, thermal, electrical, light or other energy from the electromagnetic spectrum including radio waves or sound waves. In addition to delivering one form of energy to the tissue introduced into the device, one form of energy may be transmitted to the device and then converted to another form of energy for transfer to the tissue, such as, for example, use of sound waves to produce heat in a receptor element or sink which would be in contact with the fatty tissue.

One important feature of the device, as embodied in the present invention, is the location of the energy transfer means within a cavity or channel formed by the walls of the cannula. This sheltered delivery of energy only within the inner confines of the cannula and not external the cannula, provides protection for the larger body of surrounding tissue from the effects of the energy transfer, thereby focusing the effects on the target tissue which has been drawn into the cannula and in proximity to or in contact with the energy transfer element or elements.

The presently preferred embodiment is illustrative of only one of a plurality of possible energy transferring means or elements for applying energy and only one of a plurality of possible configurations for the energy transferring means. Other orientations or combinations for applying energy and configuring energy transfer means which achieve substantially the same effect of providing energy delivery to tissue confined to the tissue drawn past entry aperture(s) in the cannula wall are also considered to be operable embodiments of the present invention. While bipolar electrical energy delivery is the preferred embodiment of the device of the present invention, as described above, it is not the only possible energy delivery means, method or configuration which meets all the unique characteristics of the device of the present invention.

Figure 1:
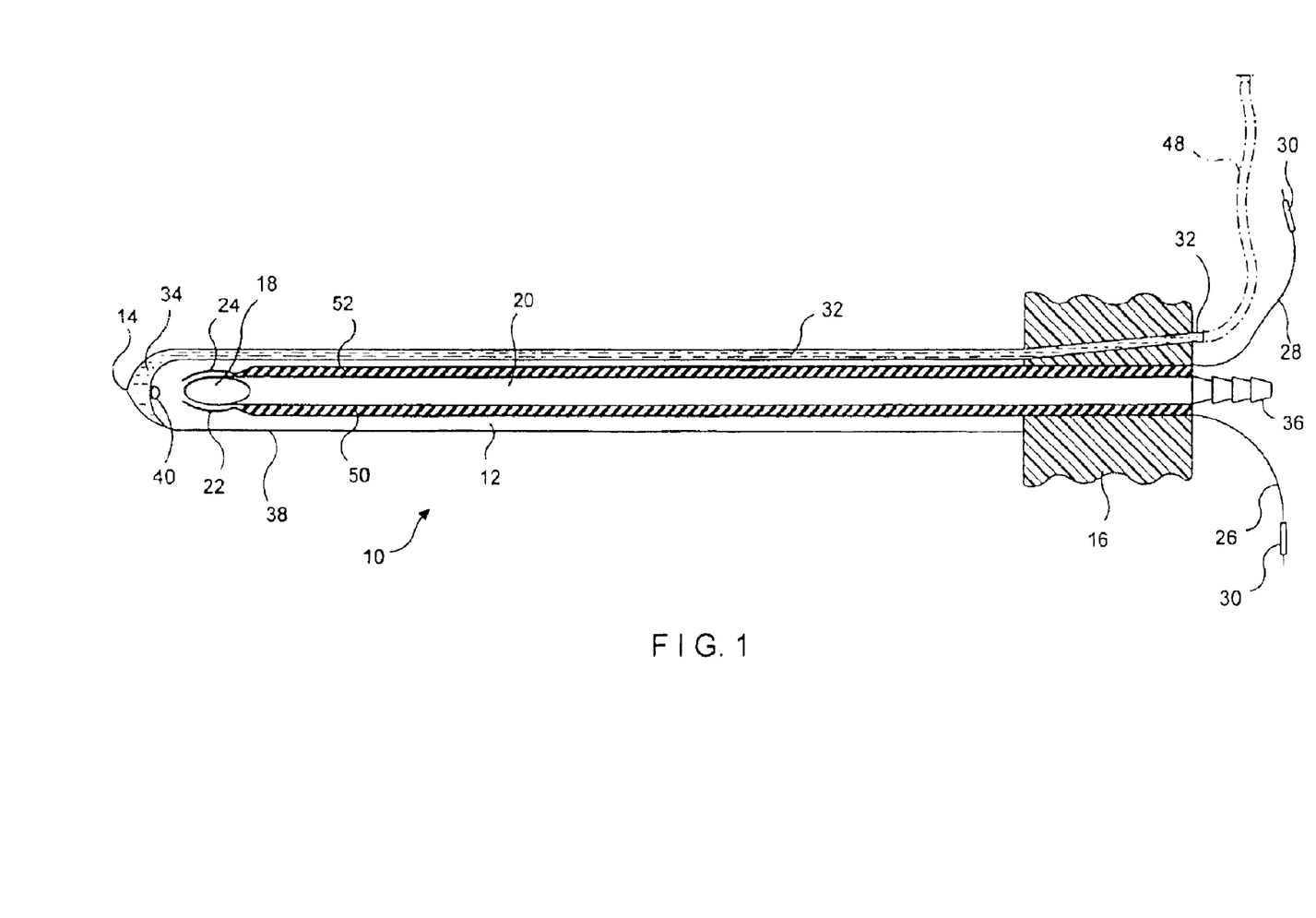
FIG. 1 is a schematic sectional view of a representative device of the present invention useful with the method of the present invention.

Turning now to FIG. 1, one embodiment of the device 10 of the present invention is schematically illustrated. The device 10, presently preferably, comprises a long cylindrical cannula 12 which has a tip or distal end 14 for insertion within biological tissue, such as, for example, adipose fatty tissue, and a proximal or handle 16 end adapted for operatively mating with electrical and irrigation means for imputing energy and irrigation fluid to the tip 14 and suction or vacuum means for evacuating adipose fatty tissue out through the cannula 12 to an external collection means (not shown). The tip 14 end includes at least one opening 18 into a lumen or hollow channel 20 within the cannula 12 which exits at an adaptation for connection to a suitable suction source (not shown).

At least one electrode and presently preferably, a pair of electrodes 22, 24 are situated beneath the opening 18 within the channel 20 positioned at a sufficient distance from one another to provide tissue coagulation, using the electrical energy generated between the electrodes 22, 24, of the tissue entering the opening 18 during suctioning or aspiration. The preferred two electrodes 22, 24 are preferably connected to the handle 16 by electrical conducting means such as, for example, electrical leads 26, 28 which are suitably shielded or insulated or both from each other and the remainder of the cannula 12 and joined to connecting means 30 positioned in the handle 16 for providing operative connection to a suitable source of electrical energy or other suitable energy source (not shown).

A second channel 32 may be positioned within the cannula 12 for providing introduction of irrigating fluid into the distal or tip end 14 of the suction channel 20 for cooling at the point of energy generation. An optional reservoir of fluid 34 may be positioned beneath the tip 14 to maximize the cooling.

As shown in FIG. 1, the device 10 of the present invention includes the hollow channel 20 operatively positioned within the cylindrical cannula 12 for application of suction to the tip 14. A suction channel adaptation means 36 for providing operative connection to the suitable source of suction is operatively positioned in the handle 16, which is kept external to the body. The adaptation means 36 may comprise, for example, suction tubing, syringe device, another intermediate adaptor coupler or other means of connection to a source of suction, aspiration or vacuum, as is known in the art.

The hollow center or channel 20 of the cylindrical cannula 12 provides a path through which suction may be applied and the irrigation fluid, blood, adipose fat and tissue debris removed from the surgical site (not shown). The channel 20 is adapted at the superficial end (the end remaining outside the body at the surgical site) to connect to suction tubing or syringe or other means of applying suction or vacuum or aspiration to the channel or lumen of the cannula. At least one and preferably more than one opening 18 is operatively formed through the outer wall 38 of the cannula 12 into the suction channel or hollow lumen 20 to allow entry of adipose fat during aspiration or suctioning at the surgical site. The openings 28 may be equidistant from the tip 14 or in a triangular pattern or all different distances from the tip. The openings may be arrayed in one portion of the circumference or spread around the circumference of the tip.

The handle 16 is adapted for providing easy one handed grip of the device 10 by a surgeon. The handle 16 provides effective means for the surgeon to direct and control the tip 14 of the device in the surgical site and advance the cannula 12 into and withdraw the cannula from the surgical site with the required control and force. As shown, the handle 16 also serves as means for connecting suction means, irrigation means and electrical energy supply means from their external sources to the cannula. The handle may be made of plastic, metal composite material or any other suitable material which is unbendable and rigid but not brittle. The handle may be inherently nonconductive or may be shielded from conduction or induction of electrical or magnetic current by additional layers or coatings externally or internally, as needed.

The cannula 12 may be made of plastic, metal, composite material or any other suitable material which is generally non-conductive or cannula may be coated with an additional layer to render it non-conductive. The optional coating layer may provide for any one or a plurality of features, such as, for example, shielding electrical conductivity, reduction of friction, and/or prevention of adherence of tissue, blood, char or debris, among others.

As shown, the tip end 14 of the cannula 12 may be shaped in a variety of ways for providing additional tissue dissection or for minimizing the profile of the cannula during passage through biological tissue.

One electrode 22 which is paired with an apposing electrode 24 is operatively positioned proximate the tip end 14 of the cannula 12. Both electrodes 22, 24 may be positioned within the suction channel 20 or on the wall of the cannula 12 at a location inside the suction channel 20.

In one preferred embodiment, the electrodes 22, 24 are located on opposite sides of the opening 18 in the cannula. In another preferred embodiment, the electrodes may be integral with the wall of the cannula 12 with an intervening insulated laminate between the electrode and the cannula 12. In yet another embodiment, the cannula wall, with or without one electrode extending into the channel may serve as one of the electrodes. In this embodiment, the apposing electrode may be on the deep wall of the suction channel or fixed in position within the channel underlying the opening. Each electrode is made from an electrical conducting material and may be coated with an additional layer of material, such as, for example, Teflon, to prevent adherence of blood, char, debris, fat or other tissue thereto during operation of the device. The electrodes may be similarly or dissimilarly shaped, including but not limited to, spatula, blade or plate shaped, circular, hemiconical, spear or shaft shaped, among others.

At least one opening 18 is formed in the outer wall 38 of the cannula 12 for providing communication between the area external the cannula 12 with the suction channel 20 within the cannula 12. The at least one or a plurality of opening(s) 18 may be circular, oval, elliptical, square, slit-like or otherwise shaped. Multiple openings may be spread evenly around the circumference of the cannula or be all located in one quadrant of the circumference or otherwise. The openings may be equidistant from the tip of the cannula or successively closer the handle end from the tip or otherwise. The possible combination of tip shapes, opening shapes, opening locations proximate the tip and around the circumference of the tip that may be employed and are intended as embodiments of the present invention are limited only to those combinations that are operable.

In one preferred embodiment, a single opening 18 is formed in the tip 14. At least one electrode pair 22, 24 is located around/beneath the at least one opening 18 or otherwise are located within the suction channel 20 in at least one location. In other embodiments of the invention, multiple pairs of electrodes may be positioned around/beneath some or all of the openings in a given embodiment of the invention. In one specific embodiment of the invention, the opening may be located at the tip or distal end of the cylindrical cannula in place of a curved or flattened closed tip, as illustrated in FIG. 1.

A second opening 40 is formed between the irrigation channel 32 and the suction channel 20, as shown in FIG. 1.

In the preferred embodiment of the device of the present invention, the second opening 40 is positioned closer to the tip 14 than the electrodes 22, 24 to allow irrigation fluid to proceed from the second opening 40 in the tip 14 and past the electrodes 22, 24 before the irrigation fluid is removed via the suction channel 20. This arrangement provides for cooling of the tip 14 and the electrodes 22, 24 thereby preventing overheating of the cannula 12 and reducing risk of creating tissue burns in the surgical site outside the cannula. Other openings between the two channels may be optionally included at any location and in any number as long as the combination provides sufficient cooling of the tip and electrodes to prevent tissue burns.

The electrical lead or wiring 26, 28 for, preferably, each electrode 22, 24 comprises such as, for example, a freestanding wire, a portion of the body of the cannula which is electrically/magnetically isolated, insulated and/or shielded from the surrounding cannula or a circuit board or any other means that functions as a continuous electrical conduit or pathway between the electrode and the energy transmitting means positioned in the handle. The leads 26, 28 are shielded or insulated by being surrounded by or covered with an electrically non-conducting coating such as, for example, plastic, composite polymer or other suitable non-conducting material. The leads may also be coiled, if traveling adjacent in the wall of the hollow channel of the cannula or may be isolated from one another by positioning on opposite sides of the circumference of the wall of the hollow channel. The physical location or arrangement or course or configuration of the leads may be geometrically or physically other than represented in FIG. 1 as long as the lead serves to provide an electrical connection between the electrodes and a power source.

The electrical jack or connecting means 30 for operatively connecting the leads 26, 28 with an outlet of the electrical power supply (not shown) is preferably formed in the handle 16. The connecting means 30 could also be in the form of a plug, jack or an outlet mounted within the handle to serve as a coupler to a power cord operatively connected to the electrical power supply.

The irrigation channel 32, shown as a hollow lumen within the cannula 12, extends from the handle 16 to the tip 14 of the cannula 12. At the tip 14 there may be an enlarged area for creating a relatively small reservoir 34 of irrigation fluid around the tip 14 and electrode area to provide more effective heat transfer to the irrigation fluid from the wall of the cannula, the tip and/or the electrodes.

At least one and possibly a large number of openings may connect the irrigation channel with the suction channel. These openings may be positioned at any location including the distal end of the cannula, around or within the electrodes, which may form an integral part of the wall of the opening, the suction channel or the irrigation channel, along the length of the irrigation channel/suction channel overlap or as may be otherwise operable. The proximal portion 48 of the irrigation channel 32 may be adapted as part of the handle 16 for connecting to standard irrigation tubing or may have a length of tubing with an appropriate connector coming out of the handle for connecting to a source of irrigation fluid (not shown).

FIG. 1 shows the path of the irrigation channel 32 relative to the cannula 12, including the optional tip reservoir 34, which will be filled with irrigation fluid during the course of normal use of the device according to the method of the present invention. FIG. 1 also shows the insulation and/or electrical or magnetic shielding 50, 52 around the electrical leads 26, 28 or between the leads and surrounding the cannula 12 and the handle 16.

One of more surfaces of the electrodes may also be insulated. In the preferred embodiments, all electrode surfaces are insulated except for the surfaces which are in apposition to the other electrode. It is an important feature of the device of the present invention that the electrodes do not make direct electrical contact with each other or with other portions of the cannula, unless they are integrated into that particular portion and are suitably insulated from surrounding, adjacent or contacting portions. Mounting points or contact points with adjacent cannula portions must have an insulation coating or element between the electrode and the adjacent portion.

Figure 2:
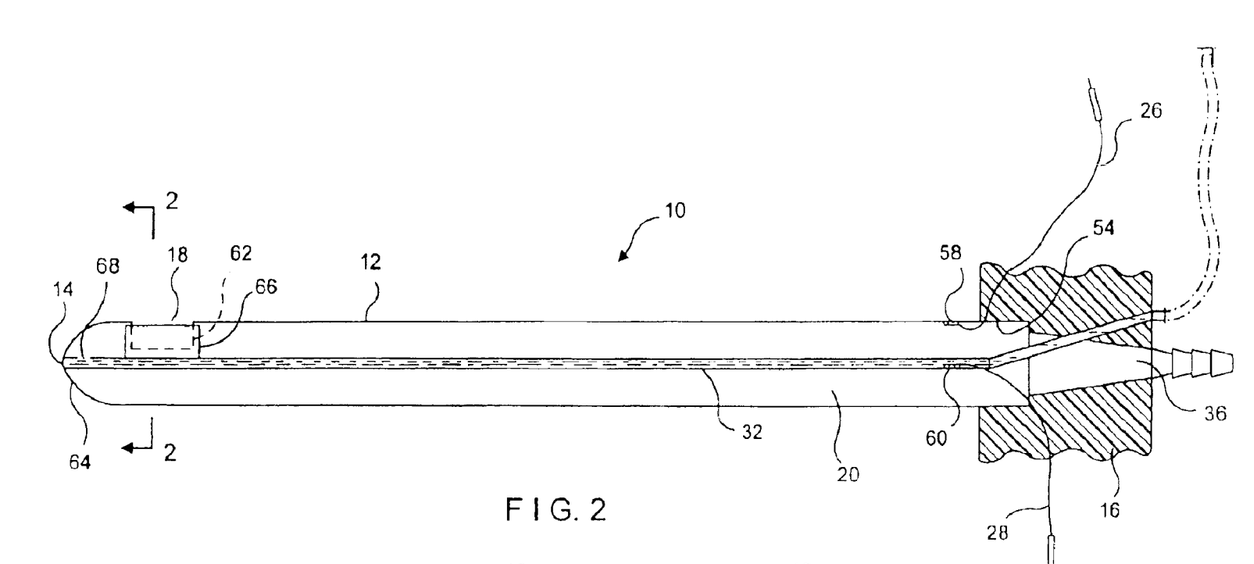
FIG. 2 is a schematic sectional view of an alternative embodiment of the device of the present invention useful with the method of the present invention.

FIG. 2 illustrates an alternative embodiment wherein the irrigation channel 32 is centrally located within the suction channel 20 of the cannula 12. In this embodiment, the irrigation channel 32 comprises an electrically conducting material which serves as one electrode and is coated with an insulating material on the inside and outside of the cannula. A portion of the cannula 12 serves as the other electrode and is made of an electrically conducting material which is coated inside and outside with an insulating material.

As stated above, the handle 16 comprises a nonconductive rigid material such as, for example, plastic. A channel 54 is formed in the handle 16 for mounting the cannula 12. The handle channel 54 provides a means for the cannula 12 suction channel 20 to exit the handle 12 such that it is operatively connected to suction tubing, syringe or other vacuum producing means 36, as is known in the art. The cannula 12 having the suction channel 20 is made of an electrically conducting material, such as, for example, metal, and is coated on both the inside and outside portions with an insulated or nonconductive material, such as, for example, plastic. The cannula having the suction channel is presently preferably cylindrically shaped and has a central circular, oval, elliptical, or oblate shaped channel the full length thereof, except for the tip 14.

The irrigation channel 32 is smaller in size than the suction channel 20 such that the irrigation channel 32 will fit within the suction channel 20, but is otherwise of similar construction. As shown, one electrode attachment point 58 is positioned in the suction channel 20 of the cannula 12 to the electrical lead 26 for connection to the electrical energy source (not shown) and the other electrode attachment point 60 is positioned in the irrigation channel 32 for connection to the electrical lead 28 and connection to the electrical energy source.

The tip 14 of the suction channel 20 may be a closed oblate, spherical, spear like, forked, sharpened, flattened, or otherwise shaped closed tip and may be an integral part of the suction channel. Alternatively, the tip 14 may be a separate, distinct part made of an insulating/non-conductive material which fits into the end 64 of the suction channel 20, closing off the channel 20 and serving as a mounting base for the irrigation channel 32 and for the suction channel, electrode extension 58.

The suction channel electrode extension 62 is positioned proximate the closed end 64 of the tip 14. The second electrode extension 66 may comprise a piece of metal or other electrically conductive material which extends out from the irrigation channel 32 in appropriate geometric relationship in apposition to but not direct contact with the suction channel electrode extension 62. The suction channel electrode extension 62 is illustrated by the stippled rectangular area which is intended to be depicted as behind the irrigation channel electrode 66 in FIG. 2. Neither electrode extension 62, 66 is insulated on the side of the electrode extension which face the other electrode extension. The other exposed surfaces of the electrode extensions are coated with an insulating material, are spaced away from surrounding structures or are surrounded by only insulated structures.

In this embodiment, the opening 18 in the cannula 12 into the suction channel 20 is positioned beneath the position of the electrode extensions. A second opening 68 is formed to effectuate fluid communication between the irrigation channel 32 and the suction channel 20. It should be noted that the two electrode extensions 62, 66 and the opening 18 in the suction channel are located between the opening 68 in the irrigation channel 32 which communicates with the suction channel 20 and the handle 16.

Figure 2A:
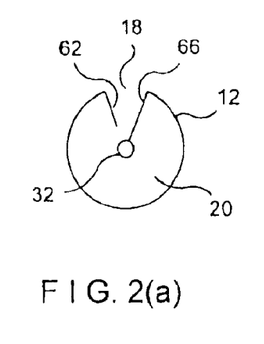
FIG. 2a is a schematic sectional view taken along line 2—2 of FIG. 2 illustrating a single opening device.
Figure 2B:
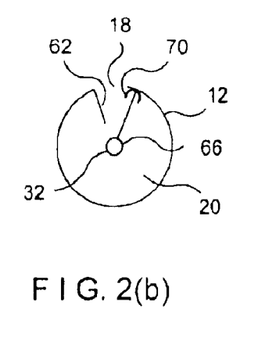
FIG. 2b is a schematic sectional view similar to that of FIG. 2a but further illustrating a stabilizing member positioned in the suction channel.

FIG. 2(a), is a cross-sectional view of a single opening device of the present invention taken along line 2—2 of FIG. 2 which further clarifies the relationship between the two electrode extensions 62, 66. It can be seen that the suction channel electrode extension 62 may be fabricated from the cannula 12 itself during manufacture by folding a portion of metal stamped or cut from the cannula to form the electrode extension 62 from the cylindrical cannula 12, leaving the portion attached on one edge of the cylindrical cannula 12. Any insulation on the apposing edge would have to be removed if insulation had been applied in this area. As shown in FIG. 2(b), a stabilizer 70 made of non-conductive material is affixed to the inner surface of the suction channel 20 to further stabilize the position of the irrigation channel electrode extension 66.

Figure 2C:
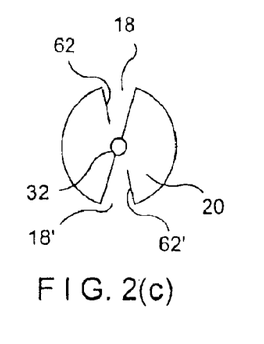
FIG. 2c is a schematic sectional view similar to that of FIG. 2a but showing a two opening device.

FIG. 2(c) illustrates an embodiment having two openings 18, 18' in the wall of the cannula 12 into the suction channel 20. As shown, the suction channel electrode extension 62 could be formed from two separate elements or one single element which is an integral part of or traverses the irrigation channel 32.

Figure 2D:
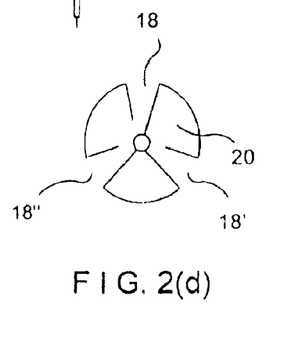
FIG. 2d is a schematic sectional view similar to FIG. 2c but illustrating a three opening device.

FIG. 2(d) illustrates an embodiment having three openings 18, 18', 18" in the wall of the cannula 12 from the suction channel 20. The arrangement of the opening 18, 18', 18" may have be sequentially positioned along one axis from the tip 14 to the handle 16, or any other arrangement found to be operative.

Figures 3, 4, 5:
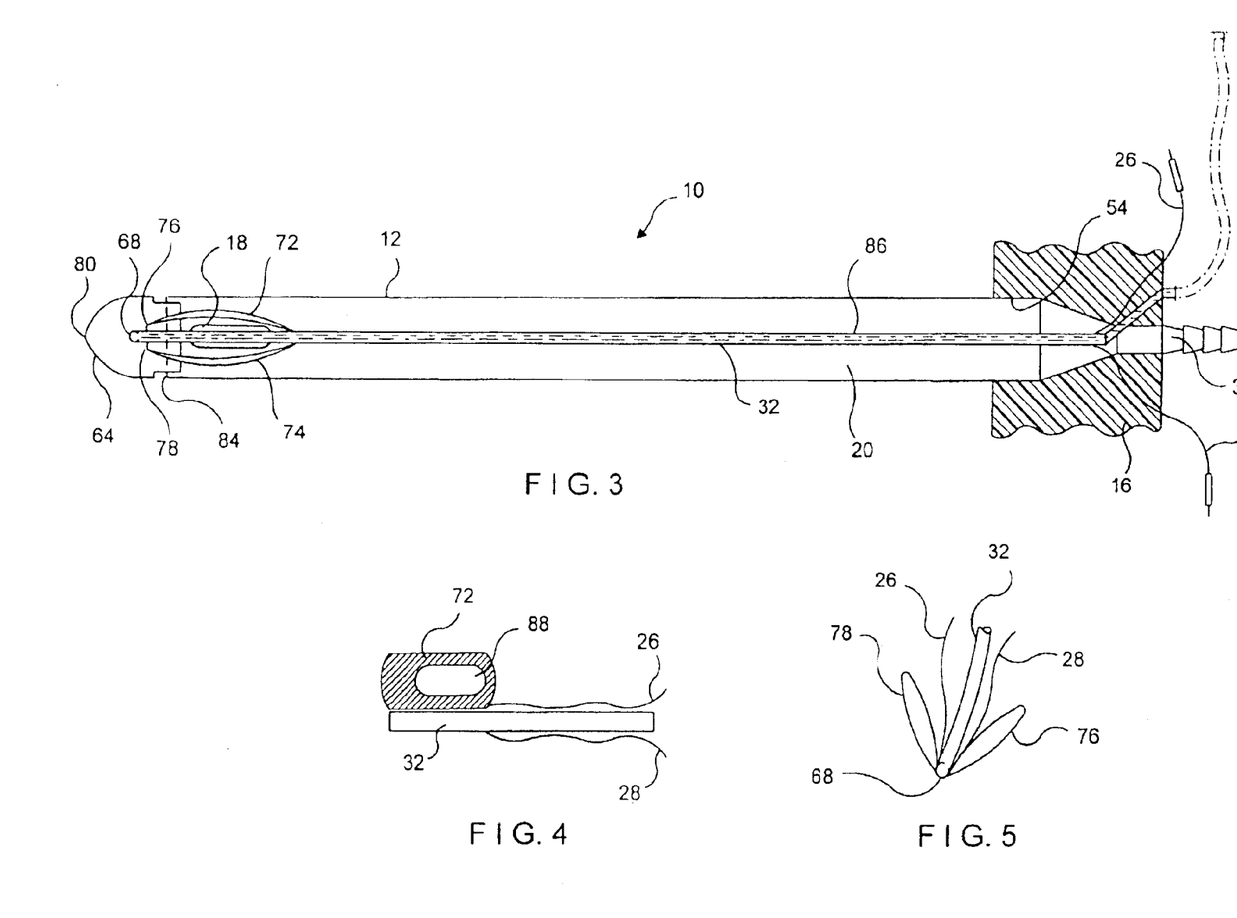
FIG. 3 is a schematic sectional view of another representative embodiment of the device useful with the method of the present invention.
FIG. 4 is a schematic sectional view of the electrode irrigation channel and the electrical leads of FIG. 3.
FIG. 5 is a schematic partial end view of the electrodes, irrigation channel and electrical lead assembly of device of FIG. 3.

FIG. 3 illustrates yet another embodiment of the present invention with the electrodes 72, 74 being separate elements which are mounted beneath the opening(s) 18 by means of fixation within mounting slots 76, 78 on the inner surface of the tip 80. The handle 16 also has a channel formed therein for providing a means for coupling the suction channel 20 with suction tubing, suction syringes or other aspiration devices 36. The suction channel comprises a cylindrical, hollow, open ended tube made of metal or other conductive material and has insulating coating operatively formed on both the inside and the outside portions of the tube. As with the previous embodiments, the handle 16 includes a means for connecting tubing or other adaptation designed to infusion tubing, irrigation pumps or others to accomplish irrigation 82.

The irrigation channel 32 is formed of a hollow tube made of plastic or metal, flexible or rigid and is operatively positioned within the suction channel 20. The at least two electrodes 76, 78 are operatively positioned on either side of the suction channel 30 distal end or tip opening 84. The two electrodes 76, 78 are operatively attached to either side of the irrigation cannula tubing 86 and are held in place by the slots 76, 78 in the tip 80. Each electrode is insulated on all sides and is attached to an electrical lead or wire 26, 28 which travels along and may be sealed onto the irrigation channel tubing 86. The electrode surface 88 that opposes the other electrode is not covered by any insulation. The separate tip 80 is preferably made of non-conducting material, such as, for example, plastic or made of metal or other material having a sufficient insulating coating and is mounted within the suction channel 20 along slots formed in the inner surface of the tip to provide consistent relative location of one electrode to another.

As in the previous embodiments, the opening 68 between the irrigation 32 and suction 20 channels provides fluid communication therebetween. As shown, the electrodes 76, 78 are situated beneath the opening 18 in the cannula 12 having the suction channel 20 therein such that the adipose tissue being drawn into the suction channel 20 through the opening 18 is in position to be acted on by the energy generated by the electrodes 72, 74.

FIG. 4 is a partial schematic cross-sectional side view illustrating the configuration of the electrode 72, the irrigation channel 32 and the electrical leads 26, 28. FIG. 5 is a partial schematic end view of the electrodes, 72, 74 irrigation channel 32 and electrical leads 26, 28 as configured in the embodiment of FIG. 3 of the device of the present invention.

The size of the opening and space between electrodes is intended to approximately match the paired electrodes of the type displayed in the embodiment of FIG. 1. Other electrode configurations are possible and the invention is not intended to be limited to the configurations shown.

Additionally, valves or controls (not shown) may be incorporated in the handle 16 or along external adaptation for connection to control application of electrical energy, suction and irrigation, as is know to those skilled in the art. These controls may provide all or none (on/off) control or provide for graded application. The controls that may be incorporated in the handle may be in addition to or instead of controls from the source devices for irrigation, suction and electrical energy.

In one preferred method of using the device of the present invention, the device is inserted through relatively small skin incisions to gain access to the subcutaneous fatty tissue to be removed. The device is maneuvered into and out of the tissue in order to traverse a large area of the fatty tissue in successive passes of the device in and out along the long axis of the device. Simultaneous with this motion by the surgeon, suction is applied through the suction channel. The strength of the suction may vary, according to individual surgeon preference and individual patient requirements. In general, the suction could be between about ten (10) and about seven hundred sixty (760) millimeters (mm) of mercury (Hg) of negative pressure, although this is not intended to be a limiting condition. This suction draws fatty tissue into the opening and between the electrodes.

Electrical energy is applied during the advancement and withdrawal of the cannula. The application of electrical energy may be continuous or discontinuous or simultaneous with suctioning or alternating with or before or after suctioning. In the preferred embodiment and the preferred method, application of electrical energy to the electrodes occurs simultaneous with suction. Monopolar or bipolar electrocautery or high frequency electrical diathermy may be used as the source of electrical energy. Other forms of electrical current or patterns of electrical energy are possible and are intended to be included in the device and method of the present invention as long as such forms are operable, as will be discussed below. Presently, the preferred modality is bipolar electrocautery. In the presently preferred method, the energy is limited to the fatty tissue contacting the energy transferring means, or electrodes 22, 24 positioned inside the suction channel 20 formed in the cannula 12.

During the surgical procedure, the amount of energy applied may be adjusted based on, including but not limited to, the size of the opening, the distance between the electrodes, and the type of tissue, among other factors. Optimum energy parameters provide complete coagulation of the tissue between the electrodes in a short period of time (less than 1 sec) without transmission of electrical energy to surrounding tissues contiguous with or external to the suction channel in the cannula. Application of the appropriate amount of energy provides for the coagulation and then removal of the adipose fat sucked into the opening without damaging skin or the fat surrounding the device.

The device of the present invention, when used with the method of the present invention, results in the rapid removal of the required amount of fat from the surgical site and improved hemostasis, among others. Bipolar electrocautery is well suited for this purpose as high powers may be used to allow rapid coagulation without significant spread beyond the area in near proximity to the electrode.

Optionally, irrigation may be used to provide cooling for the electrodes and the tip and to reduce buildup of debris around the electrodes and within the cannula. The irrigation fluid flow to the vicinity of the electrodes may be increased to a higher rate or decreased to a lower rate in order to vary the cooling effect, as required. A thermistor could be mounted in the tip of the cannula to provide for surgeon controlled or device controlled modulation of the irrigation fluid flow rate in order to maintain tip temperature below about forty (40°) degrees Centigrade (C). Possible irrigation fluids include, but are not limited to, sterile aqueous solutions of saline, lactated Ringer's solution, water, lidocaine, epinephrine, bupivucaine, sodium bicarbonate, sodium chloride or combinations of any of the above or others, as would be suitable for use in this particular type of surgery.

Use of sterile water would serve to reduce conductivity between the electrodes except when occluded by tissue itself, thus, reducing the degree of cautery effect compared with electrolyte containing solutions. Use of water would also increase cell lysis of the tissue within the cannula. Use of saline or other electrolyte solutions would increase conductivity between the two electrodes.

As should be obvious, the device of the present invention, as presently preferred, is designed for contact delivery of energy to the tissue using the energy transfer element. Along those same lines, a laser fiber could be used to deliver energy to the distal end of the cannula. At the distal end, the energy could be converted to heat using an absorbing medium in contact with the fat acting as an energy transferring element. Sapphire tip technology is an example of such a device or system where light energy from the laser fiber is converted to heat energy in the sapphire tip. The sapphire tip is then placed in contact with tissue to provide cutting, coagulation or ablation.

In the device and method of the present invention, contact means of energy transfer are presently preferred but non-contact means of energy transfer are acceptable, as long as they are operable. Also, in the present invention, if laser light were used as the energy source, it would be preferable to use a light transfer element, such as, for example, a modified fiber tip or an element coupled to the fiber tip to provide diffusion of light to the tissue or redirection of light to focus it in the "kill zone" of the domain defined for energy delivery located deep to the cannula opening.

Use of other forms of energy, such as sound, heat, light, radio waves or other forms of energy found in the electromagnetic spectrum in pulsed, continuous, discontinuous, monochromatic, polychromatic, coherent or incoherent form, although not used with the presently preferred embodiment are also intended to be considered within the scope of the present invention as long as they are operable to provide enhanced tissue coagulation disruption, removal, hemostasis or other desired surgical effects, as known to those skilled in the art. Further, the use of any of the above mentioned modes of energy delivery to a variety of energy absorbing media which alter the form or mode of the energy and then transfer the energy so altered to the tissue (i.e. act as energy absorbing and energy transferring elements) is also intended to be considered within the scope of the present invention as long as they are operable to provide the desired surgical effects.

As can be seen, utilization of the devices and methods of the present invention for suction-assisted lipectomy has met the objects of the invention and has many advantages over prior devices and methods. Specifically, less time is required to remove the fatty tissue from the surgical site as compared to other methods using previous devices; less tissue trauma is created as the energy is applied to the fatty tissue inside the cannula; the size of the visible scar at the surgical site may be reduced; a shortened recovery time may be required; the electrodes do not directly contact any tissue external the suction channel the cannula; more complete fat removal is accomplished as compared to prior devices and better hemostasis is obtained, producing less bruising, less blood loss and faster recovery as compared to prior devices and methods.

Changes and modifications in this specifically described embodiment can be carried out without departing from the scope of the invention that is intended to be limited only by the scope of the appended claims.

I claim:

1. A method for removing tissue from a body, said method comprising the steps of:
  providing a device comprising:
    a hollow cannula having at least one opening in the distal end and means for connecting the cannula to a negative pressure source at the proximal end;
    a handle, operatively connected to the cannula, for use by a surgeon to direct and control the distal end of the device in a surgical site and advance the cannula into and withdraw the cannula from the surgical site with the required control and force;
    energy transferring means, operatively positioned proximate the opening and operatively connected to an energy source, for transferring energy to tissue drawn into the cannula through the at least one opening; and
    means, operatively connected to the cannula, for delivering irrigation fluid to the vicinity of the energy transferring means;
  inserting the device through relatively small skin incisions to gain access to the tissue to be removed;
  maneuvering the device into and out of the tissue in order to traverse a large area of the tissue in successive passes of the device in and out along the long axis of the device;
  simultaneous with the maneuvering motion by the surgeon, applying suction through a suction channel formed in the cannula;
  applying energy to the energy transfer means during the advancement and withdrawal of the cannula; and irrigating to provide cooling for the energy transferring means and the opening and to reduce buildup of debris around the energy transferring means and within the cannula.

2. The method of claim 1 further comprising the step of:

varying the strength of the suction according to individual surgeon preference and individual patient requirements.

3. The method of claim 2 wherein strength of the suction is varied between about ten (10) and about seven hundred sixty (760) millimeters(mm) of mercury (Hg) of negative pressure.

4. The method of claim 1 wherein the energy applying step further comprises:

continuous or discontinuous application of energy simultaneous with suctioning or before or after suctioning.

5. The method of claim 4 wherein the energy applying step further comprises:

providing a pair of electrodes as the energy transferring means; and during the surgical procedure, adjusting the amount of energy applied based on the size of the opening, the distance between the electrodes, and the type of tissue such that complete coagulation of the tissue between the electrodes is accomplished in a short period of time without transmission of excess energy to surrounding tissues contiguous with or external to the suction means in the cannula.

6. The method of claim 1 wherein the energy applying step further comprises:

application of sufficient energy to coagulate and then remove tissue sucked into the opening without damaging skin or the tissue surrounding the device.

7. The method of claim 1 wherein the irrigating step further comprises:

selectively adjusting the irrigation fluid flow to the vicinity of the energy transferring means such that the cooling effect is selectively varied.

8. The method of claim 1 wherein the irrigating step further comprises:

operatively positioning a thermistor proximal the opening in the tip of the cannula such that tip temperature is maintained below about forty (40) degrees Centigrade (C).

9. The method of claim 1 wherein the irrigation fluids are selected from the group comprising:

sterile aqueous solutions of saline, lactated Ringer's solution, water, lidocaine, epinephrine, bupivucaine, sodium bicarbonate, sodium chloride or combinations of any of the above.

* * * * *